United States Patent
Nakano et al.

(10) Patent No.: US 11,345,885 B2
(45) Date of Patent: May 31, 2022

(54) AGENT FOR INDUCING CALLUS AND METHOD FOR INDUCING CALLUS

(71) Applicant: RIKEN, Wako (JP)

(72) Inventors: Takeshi Nakano, Wako (JP); Tadao Asami, Wako (JP); Ayumi Yamagami, Wako (JP); Hiroyuki Osada, Wako (JP); Misato Ohtani, Wako (JP); Taku Demura, Wako (JP)

(73) Assignee: RIKEN, Saitama (JP)

( * ) Notice: Subject to any disclaimer, the term of this patent is extended or adjusted under 35 U.S.C. 154(b) by 9 days.

(21) Appl. No.: 16/860,597

(22) Filed: Apr. 28, 2020

(65) Prior Publication Data

US 2020/0255797 A1   Aug. 13, 2020

Related U.S. Application Data

(62) Division of application No. 15/315,886, filed as application No. PCT/JP2015/065332 on May 28, 2015, now Pat. No. 10,676,711.

(30) Foreign Application Priority Data

Jun. 6, 2014 (JP) .................. 2014-117832

(51) Int. Cl.
*C12N 5/00* (2006.01)
*A01H 4/00* (2006.01)

(52) U.S. Cl.
CPC ........... *C12N 5/0025* (2013.01); *A01H 4/005* (2013.01)

(58) Field of Classification Search
CPC .................................................. C12N 5/0025
See application file for complete search history.

(56) References Cited

FOREIGN PATENT DOCUMENTS

| EP | 0090203 A2 | 10/1983 |
|----|------------|---------|
| EP | 2679241 A1 | 1/2014 |
| JP | 62-201572 A | 9/1987 |
| JP | 06-067668 B2 | 8/1994 |
| JP | 2002-503239 A | 1/2002 |
| JP | 2003-047463 A | 2/2003 |
| WO | WO 98/56771 A2 | 12/1998 |

OTHER PUBLICATIONS

Sleno et al (Investigating the in vitro metabolism of fipexide: characterization of reactive metabolites using liquid chromatography/mass spectrometry. Rapid Commun. Mass Spectrom. 21: 2301-2311, 2007) (Year: 2007).*
Clarke et al Agrobacterium tumefaciens-mediated transformation of poinsettia, *Euphorbia pulcherrima*, with virus-derived hairpin RNA constructs confers resistance to Poinsettia mosaic virus. Plant Cell Rep 27:1027-1038, 2008) (Year: 2008).*
Moura et al (Induction of Somatic Embryogenesis in Immature Seeds of Guava Tree cv. Paluma. Rev. Bras. Frutic, Jaboticabal—SP, v. 31, n. 2, p. 507-511, 2009). (Year: 2009).*
Liu et al (Stimulation of Adventitious Rooting in Cuttings of Four Herbaceous Species by Piperazine. Annals of Botany. 75:119-125, 1995). (Year: 1995).*
Clarke et al., "High-Frequency Transformation of *Arabidopsis thaliana* by Agrobacterium tumefaciens," Plant Molecular Biology Reporter, 1992, 10:178-189.
Hakozaki et al., "Effects of 4-Chlorophenoxyacetic Acid on the Callus and Adventition Organogenesis from Cultures Leaf Explant African Violet In Vitro," Mem. Inst. Sci. Tech. Meiji Univ., 2001, 20(1):1-8, with English synopsis on first page.
Ikeuchi, Momoko et al., "Plant Callus: Mechanisms of Induction and Repression," The Plant Cell, Sep. 2013, pp. 3159-3173, vol. 25 (15 pages).
International Search Report dated Aug. 25, 2015, in PCT/JP2015/065332.
Miroshnichenko et al., "Effects of daminozide on somatic embryogenesis from immature and mature embryos of wheat," Australian Journal of Crop Science, 2009, 3:83-94.
Moura et al., "Induction of Somatic Embryogenesis in Immature Seeds of Guava Tree cv. Paluma," Rev. Bras. Frutic. Jaboticabal—SP, 2009, 31(2):507-511.
Nakano et al., "FPX is a Novel Chemical Inducer that Promotes Callus Formation and Shoot Regeneration in Plants," Plant Cell Physiol., 2018, 59(8):1555-1567.
Office Action dated Feb. 12, 2019, in JP 2016-525126 (3 pages).
Office Action dated Feb. 6, 2020, in EP 15803135.1.
Rich et al., "Cytochrome Components of Plant Microsomes," Eur. J. Biochem., Jul. 1, 1975, 55(2):333-341.

(Continued)

*Primary Examiner* — Bratislav Stankovic
*Assistant Examiner* — Wayne Zhong
(74) *Attorney, Agent, or Firm* — Foley & Lardner LLP (57) ABSTRACT

This invention relates to an agent for inducing a callus comprising a compound represented by Formula (I) or a hydrolysis product of an amide bond thereof:

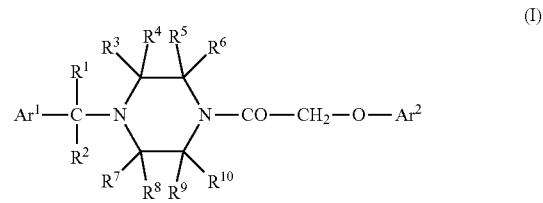

wherein $Ar^1$ represents phenyl substituted with substituent or substituents selected from alkoxy and methylenedioxy; $Ar^2$ represents phenyl substituted with halogen; $R^1$ and $R^2$ each represent hydrogen, alkyl, cyano, or carboxyl; $R^1$ and $R^2$ may together form oxo; $R^3$ to $R^{10}$ each represent hydrogen or methyl; and $R^3$ and $R^4$, $R^5$ and $R^6$, $R^7$ and $R^8$, and/or $R^9$ and $R^{10}$ may together form oxo; a method for inducing a callus and a method for plant transformation using such agent for inducing a callus.

4 Claims, 8 Drawing Sheets

(56) References Cited

OTHER PUBLICATIONS

Robledo-Paz et al., "Biotechnological Tools for Garlic Propagation and Improvement," Innovations in Biotechnology, 2012, 31-56.

Schenk et al., "Medium and techniques for induction and growth of monocotyledonous and dicotyledonous plant cell cultures," Canadian Journal of Botany, Jan. 1, 1972, 50:199-204.

Skoog et al., "Chemical Regulation of Growth and Organ Formation in Plant Tissues Cultured In Vitro," SYmp. Soc. Exp. Biol., 1957, 54:118-130.

Sleno et al., "Investigating the in vitro metabolism of fipexide: characterization of reactive metabolites using liquid chromatography/mass spectrometry," Rapid Commun. Mass Spectrom., 2007, 21:2301-2311.

Supplementary European Search Report dated Jul. 31, 2019, in EP 15803135.1.

Supplementary European Search Report dated Oct. 16, 2017, in EP 15803135.1.

Tanaka et al., "Identification of FPX, novel compound for promoting formation of plant calluses, and PPG, novel compound for promoting plant growth, and analysis of physiological action thereof," Dai 56 Kai Proceedings of the Annual Meeting of the Japanese Society of Plant Physiologists, Mar. 9, 2015, 56(Supp):307, 2P11(0727), with English translation.

Tanaka et al., "Physiological function of FPX as a novel plant callus inducible compound and PPG as a novel promoter for plant growth," Regulation of Plant Growth and Development, Oct. 1, 2014, 49(Supp):58, with English abstract.

Tanaka et al., "Structure of Fipexide Hydrochloride Monohydrate," Analytical Sciences, 2006, 22:31-32.

Tao et al., "Plant regeneration from leaf-derived callus in *Citrus grandis* (pummelo): Effects of auxins in callus induction medium," Plant Cell, Tissue and Organ Culture, May 1, 2002, 69:141-146.

Xu et al., "Callus formation from root protoplasts of *Glycine max* (soybean)," Plant Science Letters, 1982, 24:111-115.

\* cited by examiner

AGENT FOR INDUCING CALLUS AND METHOD FOR INDUCING CALLUS

CROSS-REFERENCE TO RELATED APPLICATIONS

This application is a Divisional of U.S. application Ser. No. 15/315,886, which is the National Stage application of PCT/JP2015/065332, filed May 28, 2015, which claims priority from Japanese application JP 2014-117832, filed Jun. 6, 2014.

TECHNICAL FIELD

The present invention relates to an agent for inducing a callus and a method for inducing a callus.

BACKGROUND ART

Plants have totipotency, such that they are able to form calluses from somatic cells that have been highly differentiated. If calluses are cultured under constant conditions, also, plant bodies can be reproduced through differentiation of adventitious embryos, adventitious buds, and adventitious roots. Callus culture is advantageous in the following respect; for example, 1) it has reproductive integrity; 2) it has the ability to differentiate a callus cell mass into various tissues and individuals; 3) a large quantity of homogeneous growth cells that are difficult to obtain in plants can be obtained; 4) a callus is suitable as an experimental material because of the absence of seasonal changes in the quality or quantity of cells; 5) the influence of a substance that has been added to the medium on plants can be directly observed; and 6) some plant species are easily induced to undergo genetic variation as a result of callus formation, and such plants can be used for breeding. Thus, callus culture has been extensively used for the production of useful materials, the development of new varieties, the gene introduction into plants, the reproduction of transformants, the production of artificial seeds, and other purposes.

In general, a callus is produced by a method in which a piece of plant tissue is cultured in a medium containing phytohormones (i.e., auxin and cytokinine) (Skoog, F., and Miller, C. O., 1957, Chemical regulation of growth and organ formation in plant tissue cultured in vitro, Symp. Soc. Exp. Biol., 54, 118-130). This method was established over 30 years ago, and this technique is indispensable for the production of transgenic crops at present. However, types of auxin and cytokinine to be used and the amount of auxin relative to that of cytokinine vary depending on plant species. Accordingly, it has been difficult to find adequate conditions for callus formation.

As synthetic auxins, 2,4-dichlorophenoxyacetic acid and 2,4,5-trichlorophenoxy acetic acid are known, and, concerning an analog thereof; i.e., 4-chlorophenoxyacetic acid, it was reported that the number of days required for leaf tissue culture of African violet, from implanting of explants to callus formation, and formation of adventitious shoots and adventitious roots, was reduced as a result of treatment performed at a particular concentration (Miyoshi Hakozaki et al., Effects of 4-Chlorophenoxyacetic Acid on the Callus and Adventitious Organogenesis from Cultured Leaf Explant African Violet in Vitro, Memoirs of the Institute of Science and Technology, Meiji University, 40, 1-7, 2001). However, callus formation efficiency was not high, and plant species capable of callus formation were limited.

As a 1,4-disubstituted piperazine derivative, JP H6-67668 (B) (1994) describes that N-methyl-N'-phenylacetylpiperazine, N-benzyl-N'-benzoylpiperazine, and the like are useful as decolorants against the color development system of bicolor thermal recording materials.

JP 2002-503239 (A) describes that a piperazine derivative having substituents at positions other than 1- and 4-positions of the piperazine ring is useful as an anti-inflammatory agent.

Fipexide, which is a type of a 1,4-disubstituted piperazine derivative (e.g., 1-[(p-chlorophenoxy)acetyl]-4-piperonylpiperazine or 1-(4-chlorophenoxyacetyl)-4-(1,3-benzodioxole-5-ylmethyl)piperazine), is known as an antidepressant.

Further, 1-piperonylpiperazine (1-(3,4-methylenedioxybenzyl)piperazine) and many 1-substituted piperazine derivatives as analogs thereof are commercially available as raw materials for chemical production.

However, there has been no report demonstrating that 1,4-disubstituted piperazine derivatives and 1-substituted piperazine derivatives are capable of callus induction.

SUMMARY OF THE INVENTION

Objects to Be Attained by the Invention

It is an object of the present invention to provide an agent for inducing a callus, which has a basic structure different from that of a conventional agent for inducing a callus, and a method for inducing a callus using such agent for inducing a callus.

Means for Attaining the Objects

The present invention is summarized as follows.
(1) An agent for inducing a callus comprising a compound represented by Formula (I) or a salt thereof:

(I)

wherein $Ar^1$ represents a phenyl group substituted with at least one substituent selected from among a $C_{1-6}$-alkoxy group and a substituted or unsubstituted methylenedioxy group;

$Ar^2$ represents a phenyl group substituted with 1 to 3 halogen atoms;

$R^1$ and $R^2$ each represent a hydrogen atom, a substituted or unsubstituted $C_{1-3}$-alkyl group, a cyano group, or a carboxyl group;

$R^1$ and $R^2$ may together form an oxo group;

$R^3$, $R^4$, $R^5$, $R^6$, $R^7$, $R^8$, $R^9$, and $R^{10}$ each represent a hydrogen atom or a methyl group; and

$R^3$ and $R^4$, $R^5$ and $R^6$, $R^7$ and $R^8$, and/or $R^9$ and $R^{10}$ may together form an oxo group.

(2) The agent for inducing a callus according to item (1) above, wherein the compound represented by Formula (I) or a salt thereof is fipexide or a salt thereof.

(3) An agent for inducing a callus comprising a compound represented by Formula (I-1) or a salt thereof:

(I-1)

wherein $Ar^1$, $R^1$, $R^2$, $R^3$, $R^4$, $R^5$, $R^6$, $R^7$, $R^8$, $R^9$, and $R^{10}$ are as defined above with respect to Formula (I) in item (1); and $R^{11}$ represents a hydrogen atom, a substituted or unsubstituted $C_{1-7}$hydrocarbon group, or an amidino group, and a compound represented by Formula (I-2) or a salt thereof:

HO—CO—CH$_2$—O—Ar$^2$ (I-2)

wherein $Ar^2$ is as defined above with respect to Formula (I) in item (1).
(4) The agent for inducing a callus according to item (3), wherein the compound represented by Formula (I-1) or a salt thereof is 1-piperonylpiperazine or a salt thereof and the compound represented by Formula (I-2) or a salt thereof is 4-chlorophenoxyacetic acid or a salt thereof.
(5) A method for inducing a callus comprising bringing a plant, a plant cell, a piece of plant tissue, or a plant seed into contact with the agent for inducing a callus according to any of (1) to (4) and inducing callus formation.
(6) A method for producing a callus comprising bringing a plant, a plant cell, a piece of plant tissue, or a plant seed into contact with the agent for inducing a callus according to any of items (1) to (4), inducing callus formation, and growing the callus.
(7) A callus produced by the method according to item (6).
(8) A method for plant transformation involving the use of a medium containing the agent for inducing a callus according to any of items (1) to (4) as a callus induction medium in the method for plant transformation by the *Agrobacterium* method.

Effects of the Invention

The agent for inducing a callus according to the present invention comprises, as an active ingredient, a 1,4-disubstituted piperazine derivative or a 1-substituted piperazine derivative having a basic structure different from a conventional agent for inducing a callus. Thus, such agent can be applied to a wide variety of plants.

EMBODIMENTS FOR IMPLEMENTING THE INVENTION

Hereafter, the present invention is described in detail.
The present invention relates to an agent for inducing a callus and a method for inducing a callus with the use of a compound comprising a particular type of substituted piperazine skeleton in which a nitrogen atom is substituted with $Ar^1$—C($R^1$)($R^2$)— and a phenoxyacetyl group (—CO—CH$_2$—O—$Ar^2$) in which a benzene ring is substituted with 1 to 3 halogen atoms in a molecule or with the use of two types of compounds comprising the substituted piperazine skeleton and the substituted phenoxyacetyl group in separate molecules in combination.
The correlation between the compound comprising the substituted piperazine skeleton and callus induction has not yet been reported.
Examples of halogen atoms as substituents of the substituted phenyl group represented by $Ar^2$ in Formulae (I) and (I-2) include fluorine, chlorine, and iodine atoms.
Examples of compounds comprising a phenoxyacetyl group (—CO—CH$_2$—O—$Ar^2$) with a benzene ring being substituted with 1 to 3 halogen atoms include 2,4-dichlorophenoxyacetic acid, 2,4,5-trichlorophenoxyacetic acid, and 4-chlorophenoxyacetic acid, and these compounds are known as synthetic auxins.
Examples of the $C_{1-6}$-alkoxy group as a substituent of the substituted phenyl group represented by $Ar^1$ in Formulae (I) and (I-1) include a methoxy group, an ethoxy group, a propoxy group, and an isopropoxy group, and examples of the substituted methylenedioxy group include a difluoromethylenedioxy group and a dichloromethylenedioxy group.
Examples of the substituted phenyl group represented by $Ar^1$ include a 3,4-methylenedioxyphenyl group (a 1,3-benzodioxol-5-yl group), a 2,3-methylenedioxyphenyl group (a 1,3-benzodioxol-4-yl group), a 3,4-(difluoromethylenedioxy)phenyl group (a 2,2-difluoro-1,3-benzodioxol-5-yl group), a 2,3-(difluoromethylenedioxy)phenyl group (a 2,2-difluoro-1,3-benzodioxol-4-yl group), a 3,4-methylenedioxy-5-methoxyphenyl group (a 7-methoxy-1,3-benzodioxol-5-yl group), a 3,4-dimethoxyphenyl group, and a 3,4,5-trimethoxyphenyl group, with the 3,4-methylenedioxyphenyl group (the 1,3-benzodioxol-5-yl group) being preferable.
Examples of the substituted phenyl group represented by $Ar^2$ in Formulae (I) and (I-2) include a 4-chlorophenyl group, a 2,4-dichlorophenyl group, and a 2,4,5-trichlorophenyl group, with the 4-chlorophenyl group being preferable.
Examples of the $C_{1-3}$-alkyl group represented by $R^1$ or $R^2$ in Formulae (I) and (I-1) include a methyl group, an ethyl group, a propyl group, and an isopropyl group, and such $C_{1-3}$ alkyl group may be substituted with one or more substituents selected from among, for example, an amino group, a hydroxyl group, a carboxyl group, a cyano group, a halogen atom (e.g., a fluorine, chlorine, or iodine atom), and a nitro group. $R^1$ and $R^2$ may together form an oxo group. $R^1$ and $R^2$ are preferably hydrogen atoms.

In Formulae (I) and (I-1), $R^3$, $R^4$, $R^5$, $R^6$, $R^7$, $R^8$, $R^9$, and $R^{10}$ are preferably hydrogen atoms.

Examples of the $C_{1-7}$ hydrocarbon group represented by $R^{11}$ in Formula (I-1) include: $C_{1-5}$-alkyl groups such as a methyl group, an ethyl group, a propyl group, an isopropyl group, a butyl group, an isobutyl group, a sec-butyl group, a tert-butyl group, a pentyl group, and an isopentyl group; $C_{2-5}$-alkenyl groups such as an allyl group (a 2-propen-1-yl group) and a 2-methyl-2-propen-1-yl group; $C_{2-5}$-alkynyl groups such as a propargyl group (a 2-propyn-1-yl group); and a benzyl group. Such $C_{1-7}$ hydrocarbon group may be substituted with one or more substituents selected from among, for example, an amino group, a hydroxyl group, a cyano group, a halogen atom (e.g., a fluorine, chlorine, or iodine atom), and a methoxy group.

Among the compounds represented by Formula (I), fipexide in which a substituted phenyl group represented by $Ar^1$ is a 3,4-methylenedioxyphenyl group (a 1,3-benzodioxol-5-yl group), a substituted phenyl group represented by $Ar^2$ is a 4-chlorophenyl group, and $R^1$, $R^2$, $R^3$, $R^4$, $R^5$, $R^6$, $R^7$, $R^8$, $R^9$, and $R^{10}$ are each a hydrogen atom is a commercially available compound known as an antidepressant comprising a small number of substituents. This compound is preferable from the viewpoint of availability.

Among the compounds represented by Formula (I-1), 1-piperonylpiperazine in which a substituted phenyl group represented by $Ar^1$ is a 3,4-methylenedioxyphenyl group (a 1,3-benzodioxol-5-yl group) and $R^1$, $R^2$, $R^3$, $R^4$, $R^5$, $R^6$, $R^7$, $R^8$, $R^9$, $R^{10}$, and $R^{11}$ are each a hydrogen atom is a commercially available compound comprising a small number of substituents. This compound is preferable from the viewpoint of availability.

Examples of salts of the compounds represented by Formula (I) or (I-1) include salts with inorganic acids, such as hydrochloric acid, sulfuric acid, phosphoric acid, hydrobromic acid, hydroiodic acid, nitric acid, pyrosulfuric acid, and metaphosphoric acid, and salts with organic acids, such as citric acid, benzoic acid, acetic acid, propionic acid, fumaric acid, maleic acid, tartaric acid, succinic acid, sulfonic acid (e.g., methanesulfonic acid, p-toluenesulfonic acid, or naphthalenesulfonic acid), and amino acid (e.g., glutamic acid).

Examples of salts of the compounds represented by Formula (I-2) include alkaline metal salts, such as sodium salt and potassium salt, lysine salt, and arginine salt.

The compounds represented by Formula (I) can be produced in accordance with a conventional technique, such as the method described in JP 2002-503239 A, in the manner described below:

(I-1b)  (I-1c)

(I-1a)

wherein $Ar^1$, $Ar^2$, $R^1$, $R^2$, $R^3$, $R^4$, $R^5$, $R^6$, $R^7$, $R^8$, $R^9$, and $R^{10}$ are as defined above; and $X^1$ and $X^2$ each independently represent a halogen atom (a chlorine, bromine, or iodine atom).

A compound represented by Formula (I-1a) is equivalent to a compound represented by Formula (I-1), wherein $R^{11}$ represents a hydrogen atom.

Products that can be obtained in the manner described above may be purified in accordance with a conventional technique, such as column chromatography using silica gel as a carrier, or recrystallization using methanol, ethanol, chloroform, dimethylsulfoxide, or water. Examples of eluting solvents used for column chromatography include methanol, ethanol, chloroform, acetone, hexane, dichloromethane, ethyl acetate, and a solvent mixture of any thereof.

Many of the compounds represented by Formulae (I), (I-1), and (I-2) are commercially available, and such commercially available compounds can be used in the present invention.

Examples of plants to which the present invention is applicable include: dicotyledonous plants, such as *Arabidopsis* plants, trees (e.g., *Populus* and *Eucalyptus*), rapeseed, tomato, tobacco, soybean, carrot, melon, apple, *Manihot utilissima, Spirodela polyrhiza*, and *Striga*; and monocotyledonous plants, such as *Gramineae* plants (e.g., rice, wheat, barley, maize, and *Brachypodium distachyon*) and *Liliaceae* plants (e.g., onion).

Plants, plant cells, pieces of plant tissue, or plant seeds to be implanted into media are not particularly limited, provided that they are capable of callus induction. Examples of plant tissues include shoot apex, stalk, leaf, shoot, germ cell, and root. Plants and the like to be implanted are preferably disinfected and sterilized with the use of, for example, an aqueous solution of sodium hypochlorite. Plants and the like grown by aseptic seeding are not necessarily sterilized.

The agent for inducing a callus according to the present invention can contain known additives for preparation, in addition to the active ingredients described above. Examples of known additives for preparation include an excipient, an emulsifier, and a moistening agent. The configuration of the agent for inducing a callus according to the present invention is not particularly limited, provided that such agent can be used in the art. Examples of configurations include an emulsion, a liquid, an oil solution, an aqueous solution, water dispersible powder, a flowable agent, a dusting powder, a microgranule, a granule, an aerosol, and a paste.

In the method for inducing a callus and the method for producing a callus according to the present invention, plants and the like can be brought into contact with the agent for inducing a callus according to the present invention without particular limitation. In accordance with a plant type, a target organ, a dosage form of the agent for inducing a callus, and other factors, an adequate means can be selected from among soaking, coating, spraying, and addition to the medium. To this end, plants and the like are preferably cultured in a medium containing the agent for inducing a callus according to the present invention.

Any callus induction medium may be used without particular limitation, provided that it contains (i) the compound represented by Formula (I) or a salt thereof or (ii) the compound represented by Formula (I-1) or a salt thereof and the compound represented by Formula (I-2) or a salt thereof and it is capable of callus induction.

While the concentration of the compound represented by Formula (I) or a salt thereof in the medium is not particularly limited, it is generally 5 to 200 μM and preferably 15 to 60 μM.

When the compound represented by Formula (I-1) or a salt thereof is used in combination with the compound represented by Formula (I-2) or a salt thereof, the concentration of the compound represented by Formula (I-1) or a salt thereof in the medium is not particularly limited, and it is generally 0.01 to 100 μM, and preferably 0.1 to 60 μM. While the concentration of the compound represented by Formula (I-2) or a salt thereof in the medium is not particularly limited, it is generally 0.01 to 100 μM, and preferably 0.1 to 60 μM.

Components other than the compound described above may be, for example, a saccharide, a gelling agent, or an inorganic salt, which is generally used for callus induction. Phytohormone may be added to the medium, provided that the effects of the present invention are not adversely affected.

Culture is preferably conducted under aseptic conditions. Culture is preferably carried out at 20° C. to 25° C., and light conditions are preferably set between continuous light conditions and continuous dark conditions. In general, callus induction is observed 2 to 4 weeks after the initiation of culture.

In order to grow the callus that was induced in the manner described above, for example, the medium may be exchanged with a fresh callus induction medium (i.e., agarose solid MS medium or liquid MS medium containing 0.9% sucrose) every month.

The grown callus may be redifferentiated by, for example, transferring the callus to a MS medium (0.9% agarose and 1.5% sucrose) containing auxin (indoleacetic acid) at 0.15 mg/l and cytokinine ($N^6$-2-isopentenyladenine) at 0.5 mg/l and developing a shoot (an adventitious bud) about 2 to 4 weeks thereafter.

The callus obtained according to the present invention can be used for production of a transgenic crop. For example, a callus may be prepared from a cell infected with *Agrobacterium*, or a callus may be infected with *Agrobacterium* comprising a plasmid to be introduced into a callus cell. Thereafter, a cell comprising a plasmid inserted into the chromosome may be separated and then redifferentiated to reproduce a plant. Thus, a transgenic crop that is capable of stable gene transfer can be obtained.

This description includes part or all of the content as disclosed in the description and/or drawings of Japanese Patent Application No. 2014-117832, which is a priority document of the present application.

EXAMPLES

Hereafter, the present invention is described in greater detail with reference to the examples, although the technical scope of the present invention is not limited to these examples.

Example 1

Fipexide Activity Test Using *Arabidopsis*

(1) Morphological Observation of *Arabidopsis* (Columbia) by Treatment with Fipexide Wild-type seeds of *Arabidopsis* (Columbia) were sowed in a ½ MS medium supplemented with fipexide at 0, 15, 30, or 45 μM, and morphological observation was conducted.

Figure 1:
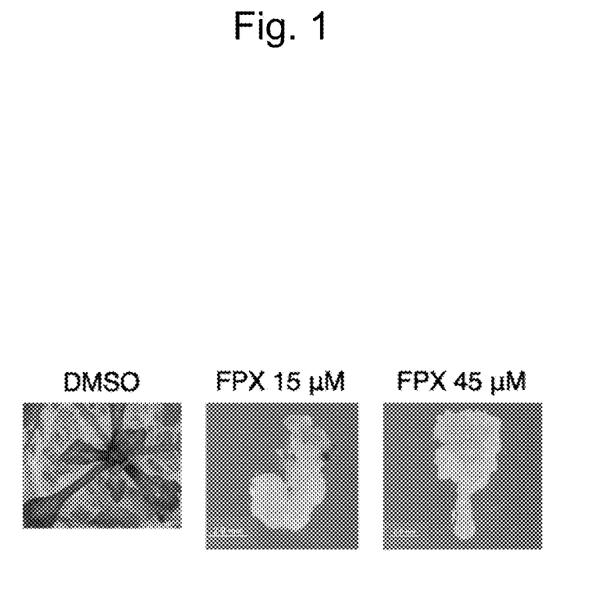
FIG. 1 shows the results of the callus induction activity test of fipexide (FPX) using *Arabidopsis*.

As a result of treatment with fipexide, callus formation was mainly observed in the root at low concentration of 15 μM and in the shoot apex at high concentration of 45 μM (FIG. 1). Since callus formation is suppressed in the root at high concentration, it was considered that the root was more sensitive to fipexide than the shoot apex and cell division was inhibited in the root.

(2) Callus Induction and Redifferentiation by Treatment with Fipexide

Figure 2A:
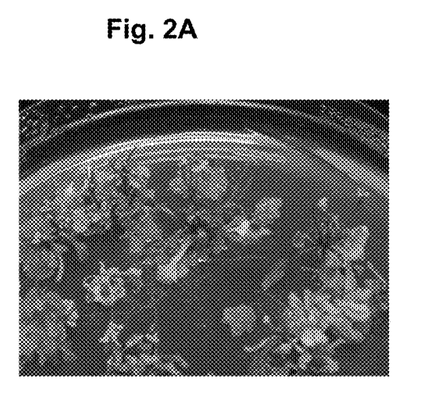
FIGS. 2A and 2B show the redifferentiation conditions as a result of treatment with fipexide (FIG. 2A) and without treatment (FIG. 2B).

The root organ of *Arabidopsis* (Columbia) was cut, treated in a ½ MS medium supplemented with fipexide at 45 μM for 2 weeks to induce a callus, and then cultured in a redifferentiation medium (auxin/cytokinine). As a result, redifferentiation was observed (FIG. 2A).

Figure 2B:
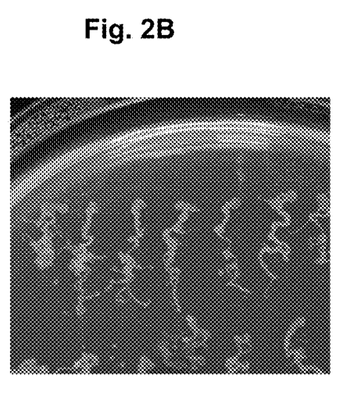

In contrast, the root organ of *Arabidopsis* (Columbia) was cut and then cultured in the redifferentiation medium without callus induction. As a result, redifferentiation was not observed (FIG. 2B).

(3) Comparison of Fipexide with Conventional Technique

Figure 3:
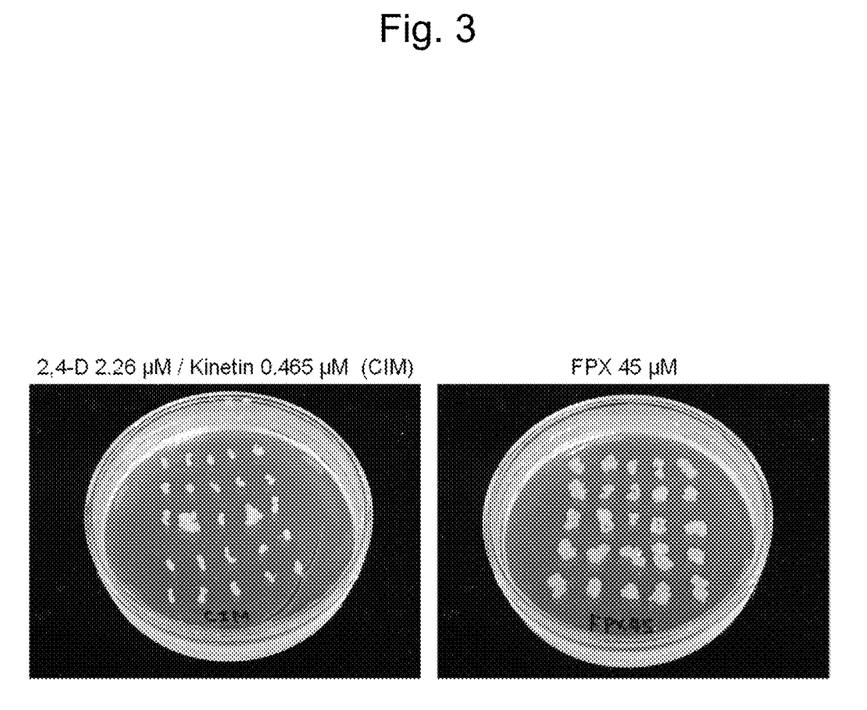
FIG. 3 shows the results of a comparison of callus induction efficiency attained with the aid of fipexide (FPX) and that attained via a conventional technique (with the aid of 2,4-dichlorophenoxyacetic acid (2,4-D)/kinetin).

Callus induction in *Arabidopsis* that was carried out at the optimized auxin/cytokinine concentration (i.e., 2,4-dichlorophenoxyacetic acid at 2.26 μM and kinetin at 0.465 μM) was compared with callus induction that was carried out at the fipexide concentration of 45 μM. As a result, callus induction efficiency of the fipexide was found to be higher than that attained at the optimized auxin/cytokinine concentration. FIG. 3 shows the conditions of the hypocotyl that had been cultured under constant lighting conditions for 87 days.

(4) Functional Analysis of Putative Fipexide Metabolites (i.e., 4-Chlorophenoxyacetic Acid and 1-Piperonylpiperazine)

Fipexide is a compound formed by an amide bond between 4-chlorophenoxyacetic acid and 1-piperonylpiperazine, and fipexide is deduced to be non-enzymatically hydrolyzed in a plant. Thus, treatment with 4-chlorophenoxyacetic acid or 1-piperonylpiperazine alone or treatment with both thereof was attempted.

*Arabidopsis* (Columbia) was allowed to germinate under weak lighting conditions for 7 days, the hypocotyl cut therefrom was placed on a ½ MS medium supplemented with 4-chlorophenoxyacetic acid and/or 1-piperonylpiperazine at 0, 5, 15, 30, 45, or 60 μM, and morphological observation thereof was conducted.

As a result, callus induction activity was observed by treatment with 4-chlorophenoxyacetic acid as with the case of treatment with fipexide. This indicates that the 4-chlorophenoxyacetic acid structure plays a key role in callus formation.

When the plant was treated with 1-piperonylpiperazine alone, in contrast, the number and the length of lateral roots were increased, and the leaf area was enlarged, although callus induction activity was not observed.

When the hypocotyl of *Arabidopsis* was treated with both 4-chlorophenoxyacetic acid and 1-piperonylpiperazine, in addition, the callus growth rate was faster than the case in which the plant was treated with 4-chlorophenoxyacetic acid alone. This indicates that cell elongation activity of 1-piperonylpiperazine additively accelerates the callus induction caused by 4-chlorophenoxyacetic acid.

Figure 4:
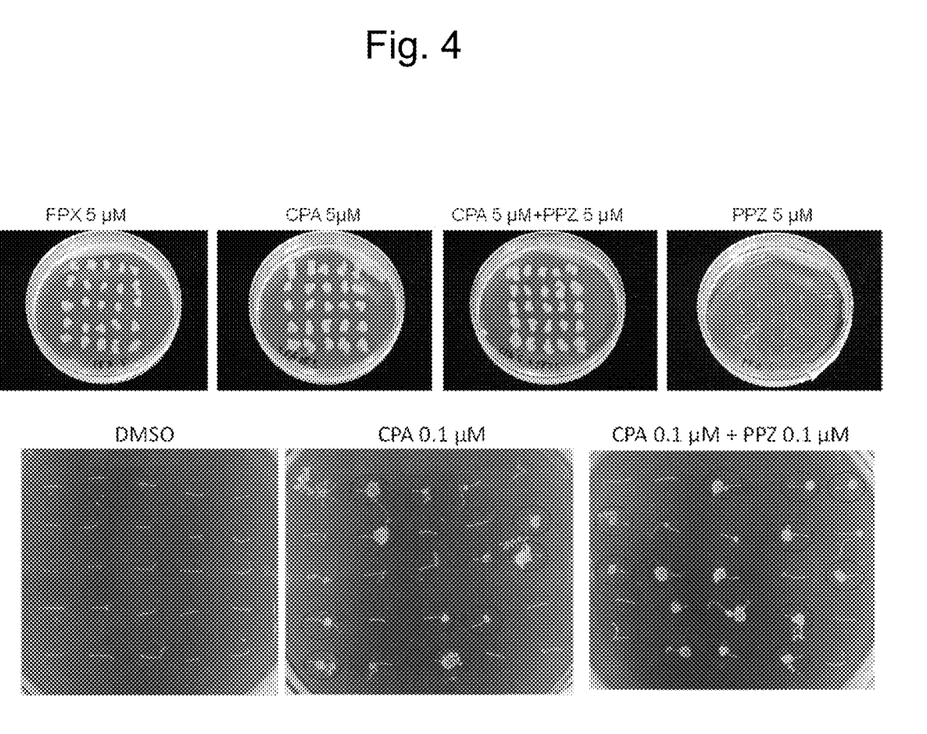
FIG. 4 shows the results of the callus induction activity tests of fipexide (FPX), 4-chlorophenoxyacetic acid (CPA) alone, 1-piperonylpiperazine (PPZ) alone, and 4-chlorophenoxyacetic acid (CPA) in combination with 1-piperonylpiperazine (PPZ).

The results are shown in FIG. 4.

Example 2

Fipexide Activity Test Using Other Plants

As with the case of *Arabidopsis* germination conditions, plants were cultured in a fipexide medium with the use of sterilized seeds. As a result, callus induction was observed in germinated rice seeds, germinated *Eucalyptus* seeds, soybean seed (Tsurunoko), tomato seed (Micro-Tom), and cucumber seed (Natsu Suzumi).

Figure 5:
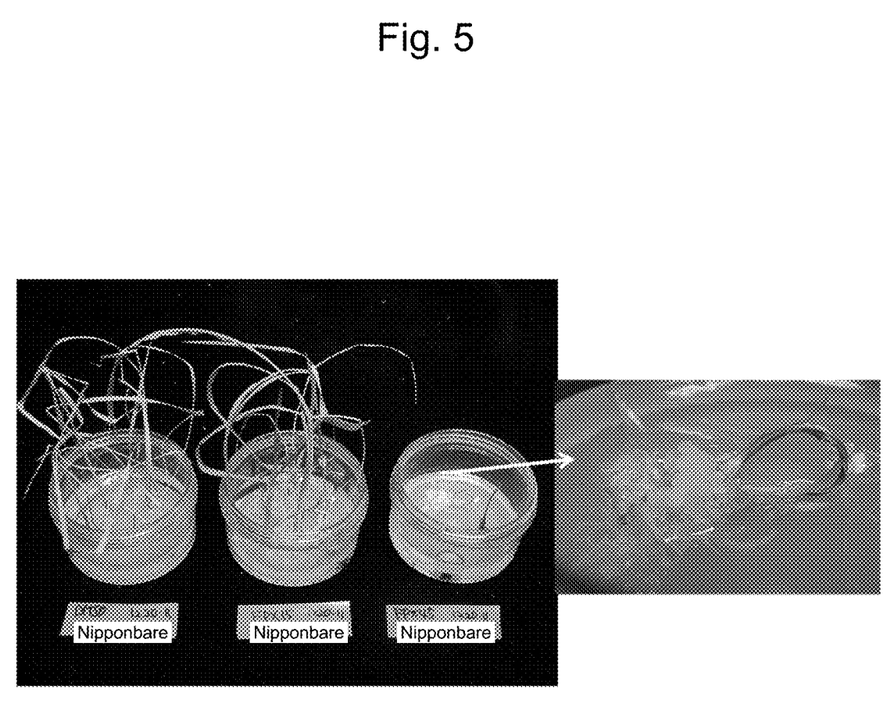
FIG. 5 shows the results of the callus induction activity test of fipexide (FPX) using the wild-type rice (Nipponbare).

FIG. 5 shows the conditions of the wild-type rice (Nipponbare) 30 days after seed germination. Callus formation was observed at fipexide concentration of 45 µM.

Figure 6:
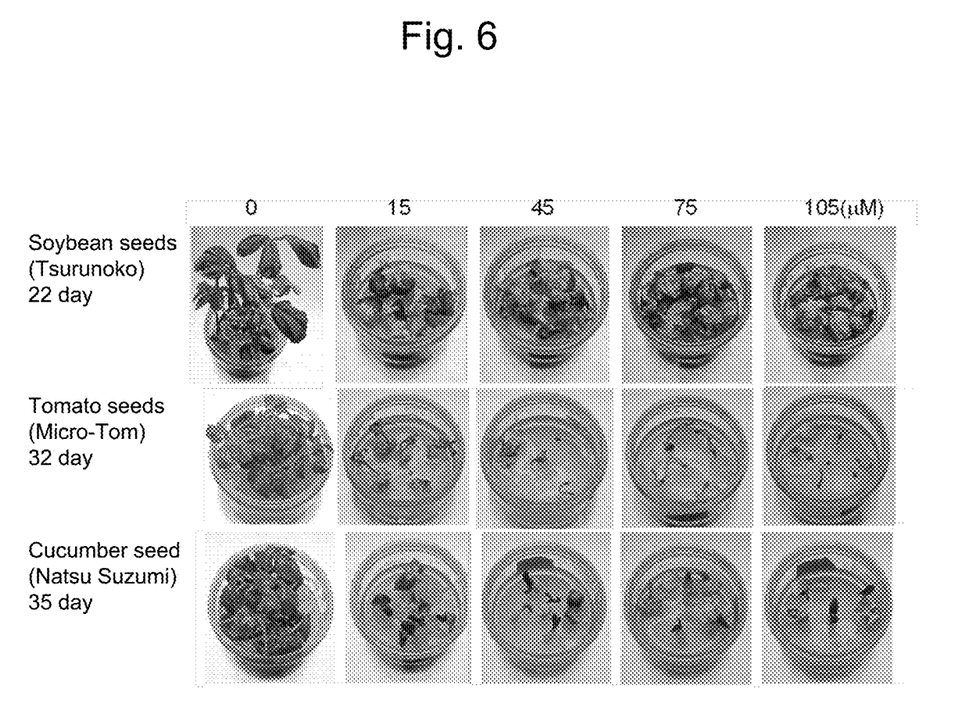
FIG. 6 shows the results of the callus induction activity test of fipexide (FPX) on soybean seed (Tsurunoko), tomato seed (Micro-Tom), and cucumber seed (Natsu Suzumi).

FIG. 6 shows the results of callus induction activity tests of fipexide (FPX) on soybean seed (Tsurunoko), tomato seed (Micro-Tom), and cucumber seed (Natsu Suzumi).

As with the case of *Arabidopsis* plants, stalks and roots of *Populus* were cultured in a fipexide medium and, as a result, callus induction was observed in the stalks and the roots of *Populus*.

The induced callus was cultured in a redifferentiation medium (i.e., a MS medium (0.9% agarose and 1.5% sucrose) containing auxin (indoleacetic acid) at 0.15 mg/l and cytokinine ($N^6$-2-isopentenyladenine) at 0.5 mg/l or a ½ MS medium (0.9% Phytoagar (agarose for plants) and 0.2% sucrose) containing 3-indolebutyric acid (IBA) at 0.1 mg/l and 6-benzylaminopurine (BAP) at 0.2 mg/l). As a result, redifferentiation was observed.

Figure 7:
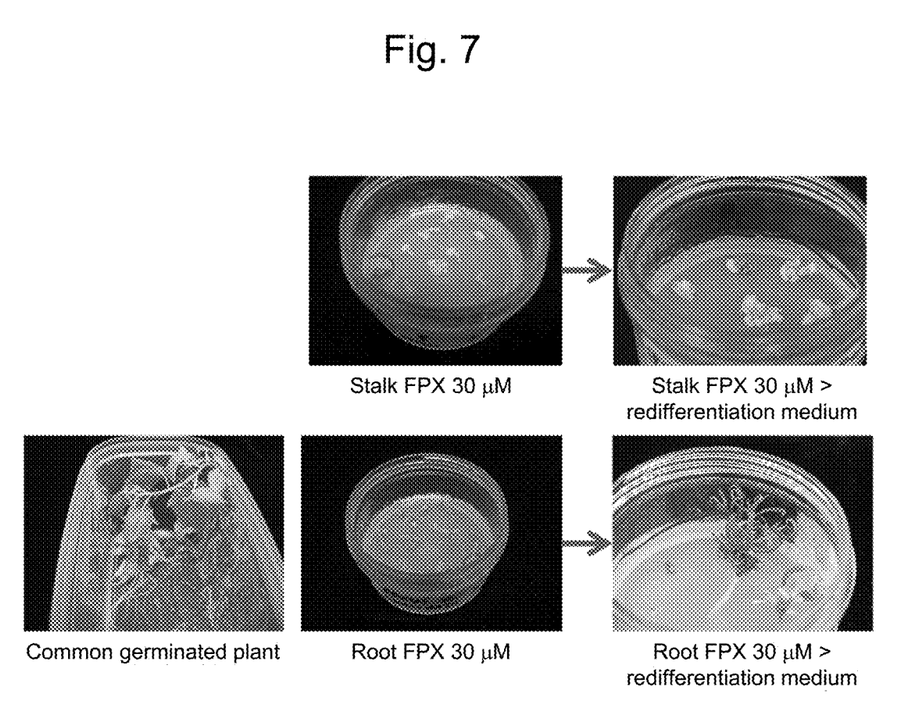
FIG. 7 shows the results of the callus induction activity test of fipexide (FPX) using wild-type *Populus*.

The conditions of the aseptic stalk (which is not the hypocotyl) and the root organ sections of wild-type *Populus* 30 days after cutting in the presence of fipexide are shown at the center of FIG. 7, and the conditions thereof 30 days after the medium was exchanged with a fresh redifferentiation medium are shown on the right of FIG. 7.

Example 3

Transformation Utilizing Callus Induction Caused by Fipexide

Under general callus induction conditions for *Populus*, callus induction was conducted with the use of fipexide instead of auxin/cytokinine, and whether or not *Agrobacterium*-infected callus was transformed was examined.

The GUS gene was introduced into a pH35GS binary vector comprising a Gateway cassette (Kubo M. et al., Genes & Dev., 19, 1855-1860, 2005) (manufactured by Inplanta Innovations Inc.; Production code: IN3-VEC17) using the Gateway system, and the resulting binary vector was used for the *Agrobacterium* method, so as to confirm infection.

The transformation procedure is described below.
1. From young plants of aseptically cultured *Populus* (*Populus tremula* x *tremuloides* T89) that had been grown in pots, stalk samples (length: 5 mm) were cut.
2. The stalk samples were cultured in the presence of *Agrobacterium* (for 3 days, in the dark, at 22° C.).
3. After *Agrobacterium* was washed away, the stalk samples were placed on MS1 medium or modified MS1 medium (containing 30 µM fipexide instead of 3-indolebutyric acid (IBA) and 6-benzylaminopurine (BAP)) and cultured at 25° C.
4. (On the fourth week, it was confirmed that many calluses were formed in modified MS1 medium containing fipexide while callus was not formed in conventional MS1 medium.)
5. Two months after the initiation of callus induction culture, 23 calluses were fixed in 90% (w/w) acetone at −30° C. overnight, the samples were washed twice with 50 mM PBS buffer (pH 7.0), and the samples were subjected to incubation in GUS substrate solution at 37° C. for 15 minutes for staining.

Figure 8:
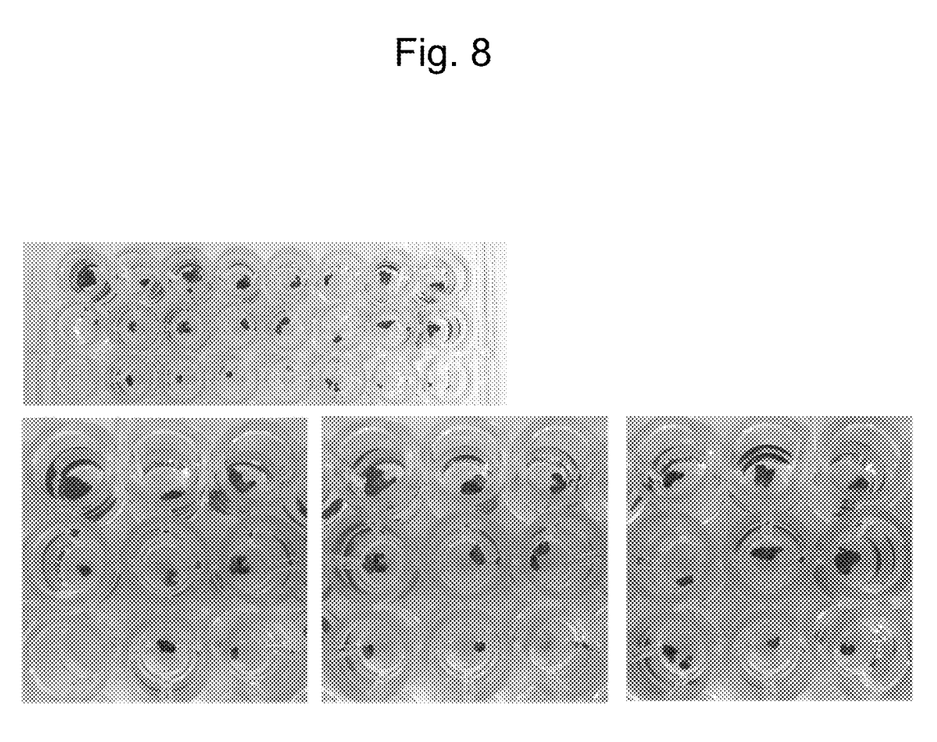
FIG. 8 shows the results of plant transformation performed by the *Agrobacterium* method that employs callus induction caused by fipexide.

As a result, GUS activity was observed in all samples. The results are shown in FIG. 8.

The compositions of the MS1 medium, the modified MS1 medium, and the GUS substrate solution are shown below.
[MS1 Medium Composition (in 1 Liter)]
4.4 g of Murashige & Skoog salt
20 g of sucrose
0.2 mg of BAP
0.1 mg of IBA
0.01 mg of TDZ (thidiazuron)
pH 5.6
[Modified MS1 Medium Composition (in 1 Liter)]
4.4 g of Murashige & Skoog salt
20 g of sucrose
30 µM of fipexide
pH 5.6
[GUS Substrate Solution Composition (in 1 Liter)]
1 mM of X-Gluc
50 mM of PBS (pH7.0)
0.1% of Triton X-100
1 mM of potassium ferricyanide
1 mM of potassium ferrocyanide Thus, it was found that callus induction caused by fipexide was applicable to a plant transformation technique by the *Agrobacterium* method.

All publications, patents, and patent applications cited herein are incorporated herein by reference in their entirety.

The invention claimed is:

1. A method for inducing a callus comprising bringing a plant, a plant cell, a piece of plant tissue, or a plant seed into contact with a combination of (a) 4-chlorophenoxyacetic acid or a salt thereof and (b) 1-piperonylpiperazine or a salt thereof, and inducing callus formation,
   wherein the combination of (a) 4-chlorophenoxyacetic acid or the salt thereof and (b) 1-piperonylpiperazine or the salt thereof accelerates callus induction relative to that induced by 4-chlorophenoxyacetic acid or the salt thereof.

2. A method for producing a callus comprising bringing a plant, a plant cell, a piece of plant tissue, or a plant seed into contact with a combination of (a) 4-chlorophenoxyacetic acid or a salt thereof and (b) 1-piperonylpiperazine or a salt thereof, inducing callus formation, and growing the callus,
   wherein the combination of (a) 4-chlorophenoxyacetic acid or the salt thereof and (b) 1-piperonylpiperazine or the salt thereof accelerates callus induction relative to that induced by 4-chlorophenoxyacetic acid or the salt thereof.

3. A method for producing a transformant comprising bringing a plant, a plant cell, a piece of plant tissue, or a plant seed into contact with 1-piperonylpiperazine or a salt thereof, and 4-chlorophenoxyacetic acid or a salt thereof in a medium containing a combination of (a) 4-chlorophenoxyacetic acid or the salt thereof and (b) 1-piperonylpiperazine or the salt thereof, producing a callus, differentiating the callus, and introducing a gene into the callus, wherein the combination of (a) 4-chlorophenoxyacetic acid or the salt thereof and (b) 1-piperonylpiperazine or the salt thereof accelerates callus induction relative to that induced by 4-chlorophenoxyacetic acid or the salt thereof.

4. A method for producing a transformant comprising bringing a transformed plant, a transformed plant cell, a transformed piece of plant tissue, or a transformed plant seed into contact with 1-piperonylpiperazine or a salt thereof, and 4-chlorophenoxyacetic acid or a salt thereof in a medium containing a combination of (a) 4-chlorophenoxyacetic acid or the salt thereof and (b) 1-piperonylpiperazine or the salt thereof, producing a callus, and differentiating the callus, wherein the transformed plant, the transformed plant cell, the transformed piece of plant tissue, or the transformed plant seed comprises an introduced gene, and wherein the combination of (a) 4-chlorophenoxyacetic acid or the salt thereof and (b) 1-piperonylpiperazine or the salt thereof accelerates callus induction relative to that induced by 4-chlorophenoxyacetic acid or the salt thereof.

* * * * *